United States Patent [19]

Someya

[11] Patent Number: 4,463,031

[45] Date of Patent: Jul. 31, 1984

[54] PROCESS FOR PREPARING A BACTERIOLOGICAL INHIBITOR FOR WATER

[76] Inventor: Nobuo Someya, 16-6, Kami-Ikebukuro 3-chome, Toshima-ku, Tokyo, Japan

[21] Appl. No.: 428,505

[22] Filed: Sep. 29, 1982

[51] Int. Cl.³ .......................... B01D 23/16; B05D 7/00
[52] U.S. Cl. .................................... 427/217; 210/501; 428/403; 428/404
[58] Field of Search ............... 427/404, 318, 319, 244, 427/307, 309, 267, 217, 287, 383.1, 383.3, 383.5, 443.2, 445; 210/501; 428/403, 404

[56] References Cited

U.S. PATENT DOCUMENTS 3,242,073  3/1966  Guebert et al. ..................... 210/501
4,407,865  10/1983  Nice .................................... 210/501

Primary Examiner—Frank Sever
Attorney, Agent, or Firm—Sughrue, Mion, Zinn, Macpeak, and Seas

[57] ABSTRACT

A process for preparing a silver-plated coral sand useful as a bacteriological inhibitor for drinking water is provided. The process comprises (1) heating desalted coral sand in an inert gas under reduced pressure; (2) thoroughly washing the resulting activated coral sand with water; (3) soaking the so washed coral sand in a silver-ammonia complex solution with heating under reduced pressure, adding a trace amount of glucose as a reducing agent to the complex solution, maintaining the soaked state to thereby effect plating the coral sand with silver; (4) evaporating the silver-plate coral sand to dryness with heating under reduced pressure; (5) thoroughly washing the silver-plated coral sand with water, and (6) then drying the silver-plated coral sand.

The silver-plated coral sand bacteriological inhibitor has a strong sterilizing power against bacteria in water and can maintain or even improve water quality over long periods of time; at the same time, the bacteriological inhibitor can change pH to a weakly alkaline side and mineralize water.

9 Claims, 2 Drawing Figures

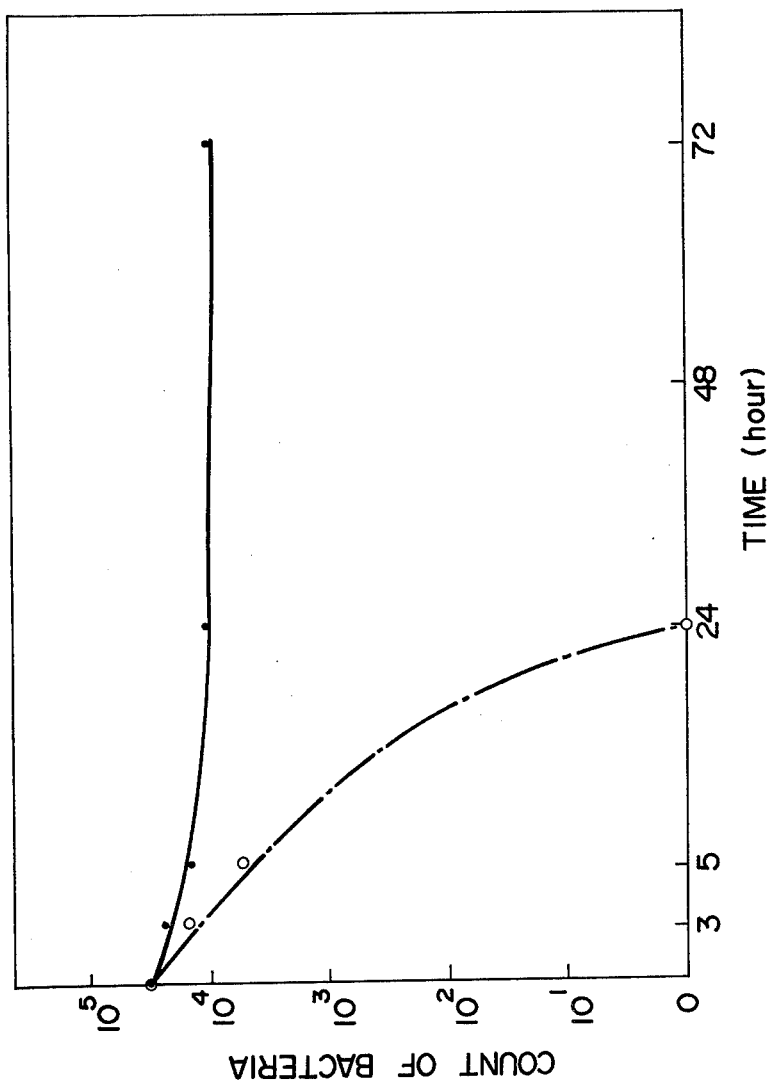

PROCESS FOR PREPARING A BACTERIOLOGICAL INHIBITOR FOR WATER

BACKGROUND OF THE INVENTION

1. Field of the Invention

The present invention relates to a process for preparing a bacteriological inhibitor for water, particularly for drinking water.

2. Development of the Invention

In recent years, the source of water supply has been contaminated by a variety of chemicals, bacteria, other microorganisms, etc. due to overpopulation or industrial wastes and, for purpose of preventing such contamination, large amounts of chlorine have been used during water purification. Accordingly, tap water supplied to domestic places has a strong bleaching powder smell. Thus, a filter is usually employed to remove the bleaching powder odor. A princple of the filter is based on filtering capability of activated charcoal with which the filter is filled up and which exhibits strong deodoring effect. The thus treated water is indeed odorless. However, tap water which is supplied in a state where it contains residual chlorine and thus possesses a sterilizing power is desalted by activated charcoal and, as a result, looses its sterilizing power. In the case where such water that has lost its anti-bacterial power is retained in the filter, bacteria in the water abruptly proliferate using as nutrition sources trace organic constituents attached to the activated charcoal packed in the filter, and, the water becomes unpotable.

As a result of extensive investigations to eliminate such disadvantages in the prior art and develop a bacteriological inhibitor for water in place of activated charcoal, it has been found that sandy coral stone or coral sand (hereafter simply referred to as "coral sand") is extremely effective as a bacteriological inhibitor for water. Further, it has also been found that coral sand plated with silver greatly improves its sterilizing power. This silver-plated coral sand is prepared by desalting coral sand by washing roughly with water, subjecting to dry distillation, again washing roughly with water (for about 3 hours) and then plating the coral sand with silver. However, it has been found that considerably large amounts of nitric acid radicals (30 to 62 ppm) are detected from the thus prepared silver-plated coral sand.

SUMMARY OF THE INVENTION

An object of the present invention is to provide a novel process for preparing a bacteriological inhibitor for water comprising silver-plated coral sand which is free from nitric acid radicals.

Another object of the present invention is to provide a process for preparing a bacteriological inhibitor for water which is capable of sterilizing and simultaneously mineralizing water.

The process of the present invention comprises (1) heating desalted coral sand in an inert gas under reduced pressure to activate the coral sand, (2) thoroughly washing the activated coral sand with water, (3) (a) soaking the washed coral sand in a silver-ammonia complex solution with heating under reduced pressure, (b) adding a trace amount of a reducing agent to the silver-ammonia complex solution, (c) maintaining the soaked state of the coral sand for a time period required to thereby plate the coral sand with silver, (4) evaporating the silver-plated coral sand to dryness with heating under reduced pressure, (5) thoroughly washing the silver-plated coral sand with water, and then (6) drying the silver-plated coral sand.

BRIEF DESCRIPTION OF THE DRAWINGS

FIG. 2 is a graph showing change in the bacteria count in tap water with passage of time, when using the silver-plated coral sand of the present invention obtained in Example 3 and activated charcoal for comparison, in which the x-axis represents a time period (hours) and the y-axis represents the bacteria count.

PREFERRED EMBODIMENTS OF THE INVENTION

Figure 1:
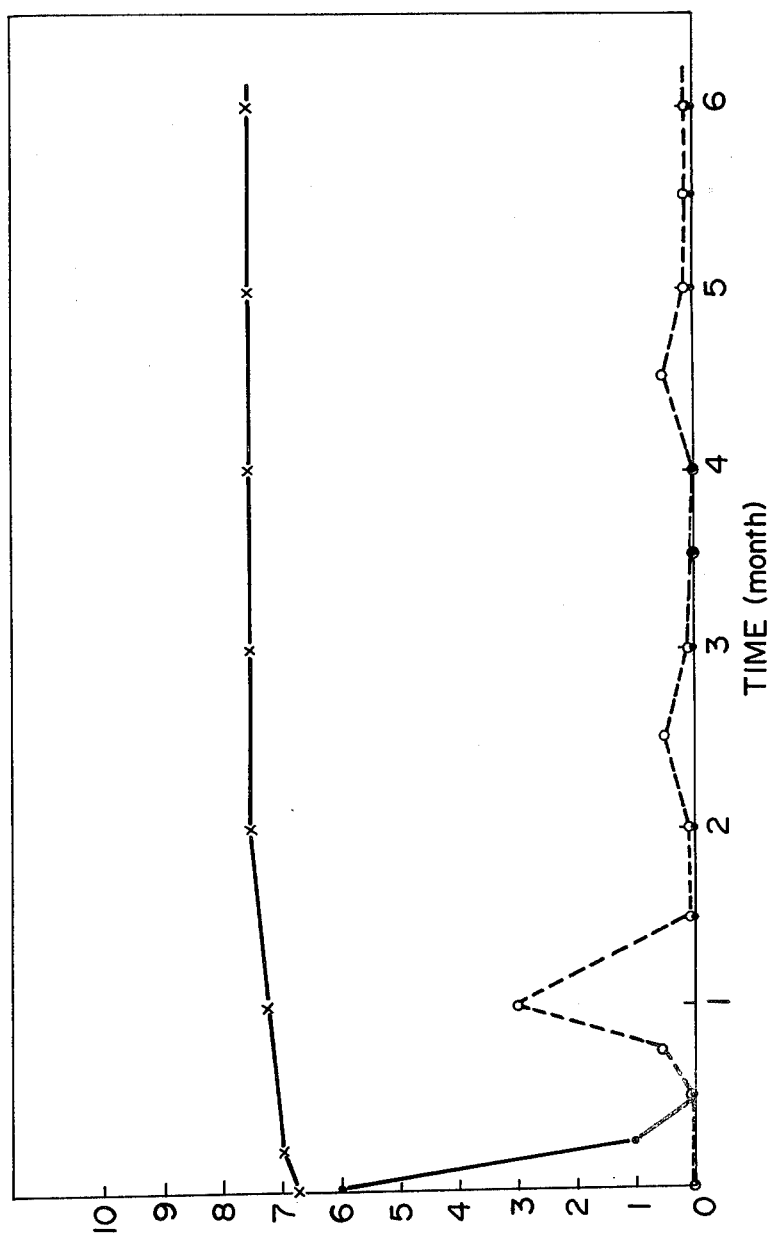
FIG. 1 is a graph showing changes in the residual chlorine content and the bacteria count in tap water as well as pH change of tap water, with passage of time, when using the silver-plated coral sand obtained in Example 3, in which the x-axis represents a time period (month) and the y-axis represents pH, the residual chlorine (numeral figure on the y-axis$\times 0.1$ ppm) and the bacteria count (numeral figure on the y-axis$\times 10$).

Coral is a hard, stony substance formed from the massed skeletons of minute marine organisms called "polyp" and contains calcium carbonate as a main ingredient, calcium phosphate as a secondary ingredient, and, as trace constituents, potassium, magnesium, iron, sodium, strontium and the like. Coral sand is prepared by crushing coral to sieve into about 20 to about 80 mesh, preferably 40 to 50 mesh. Microscopic observation indicates that coral sand possesses infinite number of pores having a diameter of from about 10 to $50\mu$. Due to pores possessed by coral sand, coral sand, has an extremely large surface area. Using coral sand as a raw material, the silver-plated coral sand is prepared by the following steps, in which reaction conditions are at ambient temperature under normal pressure, unless otherwise indicated.

Step (1)

Firstly, coral sand is desalted by washing with water. The desalted coral sand is then heated at temperatures generally in the range of from about 200° to 400° C., preferably about 350° C. for about 2 to about 4 hours, in an inert gas such as argon or nitrogen gas under reduced pressure of approximately $-20$ to $-50$ mmHg. At this step, chlorine ions which are present in coral itself are removed therefrom and the coral sand is activated.

Step (2)

After completion of Step (1), the coral sand is thoroughly washed with water. The term "thoroughly washed" refers to a state until nitric acid radicals possessed by the coral itself are not substantially detectable and such a state results from washing the activated coral sand over a time period of about 24 hours. If the washing is insufficient (for example, washing for about 3 hours), considerably high concentrations of nitric acid radicals which do not meet Water Standards are detected.

Step (3)

(a) Following the thorough washing with water, the activated coral sand is plated with silver. The silver plating is generally performed by soaking the activated coral sand in an aqueous solution of a silver-ammonia complex obtained by mixing silver nitrate and ammonia water under reduced pressure of from about −20 to about −50 mm Hg while maintaining a temperature of the solution of about 20° to about 40° C., for about 1 hours. Due to the fact that the melting point of silver is about 1000° C. whereas coral has a melting point of about 500° C., it is of practical significance to use silver for plating in the form of a silver-ammonia complex.

(b) Then, a reducing agent is added to the complex solution in a trace amount. Typical examples of reducing agents include glucose, a Rochelle salt, formaldehyde, etc. Of these reducing agents, glucose is most preferred. The reducing agent is added to reduce nitric acid radicals which might be present in a trace amounts.

(c) In such a soaked state, the system is allowed to stand at ambient temperature for about 10 to about 20 hours. In about 10 to about 20 hours, the coral sand becomes black which indicates that metallic silver is formed on the coral sand. The blackened state is an indication of the completion of the silver plating.

Step (4)

After completion of the silver plating, the coral sand is subjected to calcination at temperatures of from about 200° to 400° C. under reduced pressure of from about −20 to about −50 mm Hg to evaporate the water off the dryness.

Step (5)

Subsequently, the silver-plated coral sand is thoroughly washed with water. It is preferred to wash the silver-plated coral sand with water for at least 24 hours.

Step (6)

Finally, the silver-plated coral sand is dried by putting it in a drying room maintained at temperatures of from about 50° to 80° C. for about 4 hours.

The coral sand obtained by the above process contains 1 to 15 wt%, preferably 1 to 10 wt%, more preferably 1 to 5 wt%, of silver, based on the total weight of the silver-plated coral sand, in the form of the coral sand being covered with silver and/or silver being attached to the coral sand. Such state of silver present on the coral sand is referred to as "silver plating" herein.

The silver-plated coral sand exhibits a sterilizing effect, when it is incorporated in water, over a long period of time, e.g., for six months or longer. Further, nitric acid radicals are not detectable in water in which the silver-plated coral sand in accordance with the present invention is soaked. The silver-plated coral sand in accordance with the present invention maintains its excellent sterilization powers but does not adversely affect water quality, even when water having the silver-plated coral sand soaked therein is stored for a long period of time. The silver-plated coral sand obtained in Example 3 was soaked in water in an amount of 200 mg/l. After the water was stored for 1 year, water quality was examined against the Water Standards of the Water Law.

Results are shown in Table 1 below.

TABLE 1

| Subject Tested | Standard Value | Results |
| --- | --- | --- |
| Nitric acid- and nitrous acid-induced nitrogen | less than 10 mg/l | not detected |
| Chlorine ions | less than 200 mg/l | 17.0 mg/l |
| Organic substances (consumption of potassium permanganate) | less than 10 mg/l | 4.3 mg/l |

TABLE 1-continued

| Subject Tested | Standard Value | Results |
| --- | --- | --- |
| General bacteria | less than 100/1 ml | 0 |
| E. coli | not to be detected | not detected |
| Iron | less than 0.3 mg/l | not detected |
| Calcium, magnesium, etc. (hardness) | less than 300 mg/l | 70.0 mg/l |
| pH | 5.8–8.6 | 7.2 |
| Odor | not to be offensive | no smell |
| Taste | not to be offensive | no taste |
| Chromaticity | less than 2° | 0 |
| Turbidity | less than 5° | 0 |
| Residual chlorine | | 0.1 |

From the results above, it is obviously seen that water quality was maintained or even improved after the storage of the water for 1 year to fully meet the Water Standards, particularly noting that (1) E. coli was not detected, (2) bacteria other than E. coli was not detected, (3) no nitric acid radicals were detected and (4) offensive smells were not appreciable. The silver-plated coral sand bacteriological inhibitor in accordance with the present invention is particularly effective for the sterilization of bacteria such as Salmonella enteritidis, Staphylococcus aureus, Bacillus sabtilis, Escherichia coil, etc. For example, the bacteriological inhibitor in accordance with the present invention completely pasturized even spore-forming bacteria and cocci almost instantly contained in distilled water in a considerably high concentration, e.g., $10^3$ to $10^6$. It is assumed that such a potent sterilizing action of the silver-plated coral sand would be based on oligodynamic action of silver which is thought to be due to a strong bond formation between silver colloid and sulfur in the sulfhydryl group in cytoplasma of bacteria to inhibit a redox system, although the mechanism is not exactly known yet.

In addition, the silver-plated coral sand makes tap water mineralize and renders the pH of tap water weakly alkaline, when it is brought into contact with tap water. This is because it is assumed that the silver-plated coral sand would release calcium ions therefrom by the reaction with the residual chlorine in tap water.

Silver is harmless to humans. It has been confirmed that only less than 0.01 ppm of silver is released from the silver-plated coral sand as a bacteriological inhibitor into water and does no harm to humans.

The silver-plated coral sand obtained in accordance with the process of the present invention has many utilities, e.g., sterilization and preservation of drinking water stored in a tank, as well as enrichment of calcium ions and magnesium ions of drinking water; storage of drinking water over long periods of time; mineralization of water; sterilization of pool water; removal of the residual chlorine in tap water as well as pH control of water; purification of river water in case of emergency to prepare drinking water therefrom, etc.

The silver-plated coral sand is employed as a filtering material in a filter or by soaking a pack filled with the silver-plated coral sand in water.

The silver-plated coral sand is employed generally in an amount ranging from 100 to 400 mg/l, preferably 150 to 250 mg/l. When the silver-plated coral sand is used as a filtering material, it is preferred that filtration is performed at LV=3 to 5.

The present invention will now be described in more detail with reference to the examples below, wherein reaction or operation conditions were at ambient temperature under normal pressure, unless otherwise indicated.

EXAMPLES 1 TO 3

Coral sand obtained by crushing coral naturally occurring in the sea around the Taketomi Island in Okinawa to sieve into 40 to 50 mesh was washed with water and then heated in a water bath to effect desaltation. After the absence of chlorine was confirmed by the Mohr test, the coral sand was dried at 60° C. for about 4 hours (Step 1).

Thereafter, the coral sand was thoroughly washed with running water for about 24 hours to remove nitric acid radicals possessed by the starting coral sand itself (Step 2).

Subsequently, the thus washed coral sand was put in a dish made of a ceramic and an aqueous solution of silver-ammonia (which was obtained by mixing silver nitrate and ammonia water in an equimolar proportion) was charged in the dish. While maintaining the aqueous silver-ammonia complex solution at about 30° C. under −40 mmHg, the coral sand was soaked in the complex solution, whereby the complex solution was allowed to permeate into lattices of the coral sand (Step 3 (a)). Then, a reducing agent shown in Table 2 below was added to the complex solution in an amount also shown in Table 1 (Step 3 (b)). At this state, the system was maintained at ambient temperature for about 15 hours. 15 Hours after, the color of the coral sand changed to black (metallic silver was formed), whereby silver plating was completed (Step 3 (c)).

The thus silver-plated coral sand was heated at 350° C. under reduced pressure of −40 mmHg until the water was evaporated off to dryness (Step 4).

The coral sand was then thoroughly washed with water for about 24 hours (Step 5).

Lastly, the thus washed coral sand with silver plating was put in a drying room maintained at 65° C. for about 4 hours (Step 6).

Results are shown in Table 2 below, wherein a silver plating rate and a yield were determined as follows.

Silver Plating rate

A silver plating rate was calculated by measuring a concentration of silver in accordance with atomic extinction photometry after dissolving the silver-plated coral sand in nitric acid, evaporating the nitric acid to dryness and then dissolving the residue in diluted hydrochloric acid.

Yield

A yield was calculated based on the silver plating rate.

TABLE 2

| Example No. | Reducing Agent | Yield (%) | SPR* (%) |
|---|---|---|---|
| 1 | Rochell salt (100 g/l) | 83 | 1.2 |
| 2 | 37% formaldehyde (1.1 ml/100 ml) | 65 | 1.8 |
| 3 | glucose | | |

*SPR: silver plating rate

With the silver-plated coral sand obtained above, sterilizing action and pH were examined. In 100 ml. of distilled water, 1 g of each of the silver-plated coral sands was soaked and 50 hours after, the concentration of silver in water and pH of water were measured.

Results are shown in Table 3 below.

TABLE 3

| Example No. | Concentration of Silver (ppb) | pH |
|---|---|---|
| 1 | 70 | |
| 2 | 60 | 9.2 |

As can be seen from the results shown in Table 2, the bacteriological inhibitors of the present invention increased pH to an alkaline side.

Further, sterilizing action was examined with the bacteriological inhibitor of the present invention obtained in Example 3.

In an open container of a 20 liter volume, tap water having pH of 6.8—which contained 0.6 ppm of the residual chlorine but no bacteria—was charged. Two packs, each filled with 25 g. of the silver-plated coral sand obtained in Example 3, were soaked in the tap water. The residual chlorine content, pH and count of bacteria were measured over 6 months.

Results are shown in FIG. 1.

In the figure, the x-axis represents a time period (month) and the y-axis represents pH, the residual chlorine content (numeral figure on the y-axis×0.1 ppm) and at the same time, count of bacteria (numeral figure on the y-axis×10). The residual chlorine content is expressed by a solid line formed by connecting black points; the count of bacteria by a dotted line formed by connecting white points; and pH by a solid line formed by connecting x points.

From the results shown in FIG. 1, it can be seen that the count of bacteria did not substantially increase even after 6 months lapsed while a slight increase was observed 1 month after, notwithstanding that the residual chlorine content became zero after 2 weeks. This indicates that the silver-plated coral sand of the present invention exhibited an excellent sterilizing action. Further, pH of water was also gradually increased from 6.8 to 7.4 during storage of water for 6 months.

In order to examine sterilizing action against *E. coli*, a test water was prepared by boiling tap water (by which the residual chlorine was removed from tap water) and then adding sewage effluent to the boiled tap water to thereby inoculate *E. coli*.

Two kinds of test water containing different counts of *E. coli* were poured into a column packed with the silver-plated coral sand (45 mesh, bulk density of 1.21 g/cc) obtained in Example 3 at SV=3. At definite time intervals, the count of *E. coli* was determined by the desoxycholate culture method.

Results are shown in Table 4.

TABLE 4

| | | Count of *E. coli* | |
|---|---|---|---|
| Time (hr.) | Amount of Effluent (ml/hr.) | Non-Treated Water | Treated Water |
| 0.25 | 80 | 21300 | 0 |
| 1.0 | 83 | 21300 | 2 |
| 3.0 | 80 | 28500 | 32 |
| 6.0 | 88 | 22500 | 600 |

As is clearly seen from the results in Table 3, there was no substantial proliferation of *E. coli* when the *E. coli* containing water was passed through the column packed with the silver-plated coral sand; whereas the count of E. coli increased seriously in water where no bacteriological inhibitor was used.

The sterilizing action of the bacteriological inhibitor obtained in the process of the present invention was compared with that of activated charcoal.

In tap water—to which sewage was added and which contained $5.0 \times 10^4$ of E. coli—, 25 g of the silver-plated coral sand obtained in Example 3 was soaked and the E. coli count was measured with the passage of time.

For comparison, 25 g of activated charcoal was used as a bacteriological inhibitor for tap water having the same count of E. coli therein and the same procedure was repeated with the activated charcoal.

Results are shown in FIG. 2, in which a solid curve shows the change of the E. coli count in tap water in the case of using activated charcoal for comparison, and, a dot-and-chain curve shows the change in the E. coli count in the case of using the silver-plated coral sand in accordance with the present invention as a bacteriological inhibitor.

As can be clearly seen from the results shown in FIG. 2, the bacteriological inhibitor in accordance with the present invention had a potent sterilization action against E. coli and 24 hours after, no E. coli was detected; whereas, activated charcoal merely prevented proliferation of E. coli with no sterilization action against E. coli.

While the invention has been described in detail, and with reference to specific embodiments thereof, it will be apparent to one skilled in the art that various changes and modifications can be made therein without departing from the spirit and scope thereof.

What is claimed is:

1. A process for preparing a bacteriological inhibitor comprising silver-plated coral sand which comprises heating desalted coral sand in an inert gas under reduced pressure to activate said coral sand; thoroughly washing said activated coral sand with water to provide activated coral sand substantially free of nitric acid radicals; soaking so washed coral sand in a nitric acid radical-free silver-ammonia complex solution with heating under reduced pressure, adding a trace amount of a reducing agent to said silver-ammonia complex solution, maintaining the soaked state of said coral sand for a time period required to thereby plate said coral sand with silver; evaporating said silver-plated coral sand to dryness with heating under reduced pressure; thoroughly washing said silver-plated coral sand with water, and then drying said silver-plated coral sand to provide a substantially nitric acid radical-free bacteriological inhibitor.

2. The process of claim 1 wherein said heating in an inert gas is at temperatures ranging from about 200° to about 400° C. under reduced pressure of from $-20$ to $-50$ mmHg.

3. The process of claim 1 wherein said thorough washing with water is performed for at least about 24 hours.

4. The process of claim 1 wherein said reducing agent is selected from the group consisting of a Rochelle salt, formaldehyde and glucose.

5. The process of claim 1 wherein said inert gas is selected from the group consisting of argon and nitrogen.

6. The process of claim 1 wherein said soaking is performed firstly under conditions at temperatures ranging from about 20° to 40° C. for about 1 hour under a reduced pressure ranging from $-20$ to $-50$ mmHg, and, after adding the reducing agent to the complex solution, maintaining the soaked state at ambient temperature for about 10 to about 20 hours.

7. The process of claim 1 wherein said heating for evaporating to dryness is performed at temperatures ranging from about 200° to 400° C. under a reduced pressure of from about $-20$ to about $-50$ mmHg.

8. The process of claim 1 wherein said drying is performed at temperatures ranging from about 50° to about 80° C. for about 4 hours.

9. The process of claim 1 wherein said silver is plated on the coral sand in an amount of 1 to 15 wt% based on the total weight of said silver-plated coral sand.

* * * * *